US012558520B2

(12) United States Patent
Gupta

(10) Patent No.: US 12,558,520 B2
(45) Date of Patent: Feb. 24, 2026

(54) INTRAVENOUS CANNULA

(71) Applicant: MedSource Labs, LLC, Chanhassen, MN (US)

(72) Inventor: Neeraj Gupta, Gurgaon (IN)

(73) Assignee: MedSource Labs, LLC, Chaska, MN (US)

( * ) Notice: Subject to any disclaimer, the term of this patent is extended or adjusted under 35 U.S.C. 154(b) by 83 days.

(21) Appl. No.: 17/551,278

(22) Filed: Dec. 15, 2021

(65) Prior Publication Data

US 2022/0249810 A1     Aug. 11, 2022

(30) Foreign Application Priority Data

Feb. 10, 2021     (IN) ............................. 202111005687

(51) Int. Cl.
*A61M 25/06*        (2006.01)
*A61M 25/00*        (2006.01)

(52) U.S. Cl.
CPC .... *A61M 25/0618* (2013.01); *A61M 25/0097* (2013.01)

(58) Field of Classification Search
CPC .......... A61M 25/0618; A61M 25/0612; A61M 25/0631; A61M 25/0625; A61M 2039/062
See application file for complete search history.

(56) References Cited

U.S. PATENT DOCUMENTS 4,022,191 A     5/1977   Jamshidi
4,269,186 A     5/1981   Loveless et al.
4,747,831 A     5/1988   Kulli
4,762,516 A     8/1988   Luther et al.
(Continued)

FOREIGN PATENT DOCUMENTS

AU        2002340363 B2      8/2008
CA          2178267 A1      12/1996
(Continued)

OTHER PUBLICATIONS

International Search Report and Written Opinion issued in International Application No. PCT/US2023/060560, mailed on Jun. 2, 2023, 10 pages.
(Continued)

*Primary Examiner* — Courtney B Fredrickson
*Assistant Examiner* — Kayla M. Turkowski
(74) *Attorney, Agent, or Firm* — Dorsey & Whitney LLP

(57)         ABSTRACT
The present disclosure discloses an intravenous cannula that includes a catheter hub and tubular valve member adapted to allow a needle member to pass through. The valve member is defined with slits that allow the needle to pass through. Further, a valve closure member and needle guard assembly are provided, both adapted to close passage for fluid flow and prevent blood flow from the punctured vein of a subject. The needle guard assembly includes a body portion. A safety clip locks onto a flange defined in the body, and in a biased condition allows a needle to extend through the body and hub. Upon withdrawal of the needle from a proximal end of the hub, a safety pin disengages from the flange and arrests the tip portion of the needle within the device, thereby preventing needle prick injury upon withdrawal of the needle member from the hub.

9 Claims, 7 Drawing Sheets

(56)                  References Cited

U.S. PATENT DOCUMENTS

| | | | |
|---|---|---|---|
| 4,778,453 A | 10/1988 | Lopez |
| 4,832,696 A | 5/1989 | Luther et al. |
| 4,834,718 A | 5/1989 | Mcdonald |
| 4,846,805 A | 7/1989 | Sitar |
| 4,878,902 A | 11/1989 | Wanderer |
| 4,887,998 A | 12/1989 | Martin et al. |
| 4,897,083 A | 1/1990 | Martell |
| 4,917,668 A | 4/1990 | Haindl |
| 4,929,241 A | 5/1990 | Kulli |
| 4,932,940 A | 6/1990 | Walker et al. |
| 4,944,725 A | 7/1990 | Mcdonald |
| 4,944,728 A | 7/1990 | Carrell et al. |
| 4,950,252 A | 8/1990 | Luther et al. |
| 4,952,207 A | 8/1990 | Lemieux |
| 4,964,854 A | 10/1990 | Luther |
| 5,000,740 A | 3/1991 | Ducharme et al. |
| 5,002,536 A | 3/1991 | Thompson et al. |
| 5,013,304 A | 5/1991 | Russell et al. |
| 5,030,205 A | 7/1991 | Holdaway et al. |
| 5,078,694 A | 1/1992 | Wallace |
| 5,092,845 A | 3/1992 | Chang |
| 5,098,410 A | 3/1992 | Kerby et al. |
| 5,108,379 A | 4/1992 | Dolgin et al. |
| 5,120,319 A | 6/1992 | Van Heugten |
| 5,135,504 A | 8/1992 | McLees |
| 5,156,599 A | 10/1992 | Ranford et al. |
| 5,195,974 A | 3/1993 | Hardy |
| 5,195,992 A | 3/1993 | Dudar et al. |
| 5,205,829 A | 4/1993 | Lituchy |
| 5,215,525 A | 6/1993 | Sturman |
| 5,215,528 A | 6/1993 | Purdy et al. |
| RE34,416 E | 10/1993 | Lemieux |
| 5,300,045 A | 4/1994 | Plassche |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,409,461 A | 4/1995 | Steinman |
| 5,419,766 A | 5/1995 | Chang et al. |
| 5,423,766 A | 6/1995 | Cesare |
| 5,533,974 A | 7/1996 | Gaba |
| 5,558,651 A | 9/1996 | Crawford et al. |
| 5,562,631 A | 10/1996 | Bogart |
| 5,599,310 A | 2/1997 | Bogert |
| 5,601,532 A | 2/1997 | Gaba |
| 5,601,535 A | 2/1997 | Byrne et al. |
| 5,601,536 A | 2/1997 | Crawford et al. |
| 5,611,781 A | 3/1997 | Sircom et al. |
| 5,662,610 A | 9/1997 | Sircom |
| 5,676,658 A | 10/1997 | Erskine |
| 5,688,249 A | 11/1997 | Chang et al. |
| 5,690,619 A | 11/1997 | Erskine |
| 5,695,474 A | 12/1997 | Daugherty |
| 5,697,907 A | 12/1997 | Gaba |
| 5,702,367 A | 12/1997 | Cover et al. |
| 5,713,876 A | 2/1998 | Bogert et al. |
| 5,800,395 A | 9/1998 | Botich et al. |
| 5,810,785 A | 9/1998 | Bogert et al. |
| 5,830,189 A | 11/1998 | Chang |
| 5,853,393 A | 12/1998 | Bogert |
| 5,879,337 A | 3/1999 | Kuracina et al. |
| 5,911,705 A | 6/1999 | Howell |
| 6,004,294 A | 12/1999 | Brimhall et al. |
| 6,050,976 A | 4/2000 | Thorne et al. |
| 6,077,244 A | 6/2000 | Botich et al. |
| 6,117,108 A | 9/2000 | Woehr et al. |
| 6,203,527 B1 | 3/2001 | Zadini et al. |
| 6,217,556 B1 | 4/2001 | Ellingson et al. |
| 6,221,047 B1 | 4/2001 | Greene et al. |
| 6,280,419 B1 | 8/2001 | Vojtasek |
| 6,287,278 B1 | 9/2001 | Woehr et al. |
| 6,287,317 B1 | 9/2001 | Makower et al. |
| 6,379,337 B1 | 4/2002 | Mohammad M. B. B. S. |
| 6,443,929 B1 | 9/2002 | Kuracina et al. |
| 6,461,362 B1 | 10/2002 | Halseth et al. |
| 6,491,707 B2 | 12/2002 | Makower et al. |
| 6,533,759 B1 | 3/2003 | Watson et al. |
| 6,582,402 B1 | 6/2003 | Erskine |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,620,136 B1 | 9/2003 | Pressly et al. |
| 6,623,458 B2 | 9/2003 | Woehr et al. |
| 6,629,957 B1 | 10/2003 | Wiklund |
| 6,629,959 B2 | 10/2003 | Kuracina et al. |
| 6,652,490 B2 | 11/2003 | Howell |
| 6,689,102 B2 | 2/2004 | Greene |
| 6,695,814 B2 | 2/2004 | Greene et al. |
| D491,266 S | 6/2004 | Cindrich et al. |
| 6,749,588 B1 | 6/2004 | Cindrich et al. |
| 6,796,962 B2 | 9/2004 | Ferguson et al. |
| 6,860,871 B2 | 3/2005 | Kuracina et al. |
| 6,872,193 B2 | 3/2005 | Shaw et al. |
| 6,893,423 B2 | 5/2005 | Denolly |
| 6,902,546 B2 | 6/2005 | Ferguson |
| 6,942,652 B1 | 9/2005 | Pressly et al. |
| 6,972,002 B2 | 12/2005 | Thorne |
| 6,979,333 B2 | 12/2005 | Hammerslag |
| 6,981,965 B2 | 1/2006 | Luther et al. |
| 6,995,814 B2 | 2/2006 | Kanatsu |
| 7,014,622 B1 | 3/2006 | Pressly et al. |
| 7,037,292 B2 | 5/2006 | Carlyon et al. |
| 7,179,244 B2 | 2/2007 | Smith et al. |
| 7,186,239 B2 | 3/2007 | Woehr |
| 7,255,685 B2 | 8/2007 | Pressly, Sr. et al. |
| 7,264,613 B2 | 9/2007 | Woehr et al. |
| 7,303,547 B2 | 12/2007 | Pressly et al. |
| 7,341,573 B2 | 3/2008 | Ferguson et al. |
| 7,344,516 B2 | 3/2008 | Erskine |
| 7,347,853 B2 | 3/2008 | Difiore et al. |
| 7,413,562 B2 | 8/2008 | Ferguson et al. |
| 7,500,965 B2 | 3/2009 | Menzi et al. |
| D592,302 S | 5/2009 | Stokes et al. |
| 7,534,227 B2 | 5/2009 | Kulli |
| 7,604,616 B2 | 10/2009 | Thoresen et al. |
| 7,611,499 B2 | 11/2009 | Woehr et al. |
| 7,625,360 B2 | 12/2009 | Woehr et al. |
| 7,632,243 B2 | 12/2009 | Bialecki et al. |
| 7,658,725 B2 | 2/2010 | Bialecki et al. |
| 7,678,080 B2 | 3/2010 | Shue et al. |
| 7,699,807 B2 | 4/2010 | Faust et al. |
| 7,736,342 B2 | 6/2010 | Abriles et al. |
| 7,753,877 B2 | 7/2010 | Bialecki et al. |
| 7,753,887 B2 | 7/2010 | Botich et al. |
| 7,785,296 B2 | 8/2010 | Muskatello et al. |
| 7,828,774 B2 | 11/2010 | Harding et al. |
| 7,951,121 B2 | 5/2011 | Weaver et al. |
| 7,963,948 B2 | 6/2011 | Melsheimer |
| 7,972,313 B2 | 7/2011 | Woehr et al. |
| 8,062,252 B2 | 11/2011 | Alheidt et al. |
| 8,070,725 B2 | 12/2011 | Christensen |
| 8,105,288 B2 | 1/2012 | Keyser et al. |
| 8,133,206 B2 | 3/2012 | Greene et al. |
| 8,172,805 B2 | 5/2012 | Mogensen et al. |
| 8,211,070 B2 | 7/2012 | Woehr et al. |
| 8,235,946 B2 | 8/2012 | Molgaard-Nielsen |
| 8,251,950 B2 | 8/2012 | Albert et al. |
| 8,257,322 B2 | 9/2012 | Koehler et al. |
| 8,282,605 B2 | 10/2012 | Tan et al. |
| 8,308,685 B2 | 11/2012 | Botich et al. |
| 8,308,691 B2 | 11/2012 | Woehr et al. |
| 8,328,762 B2 | 12/2012 | Woehr et al. |
| 8,333,735 B2 | 12/2012 | Woehr et al. |
| 8,337,463 B2 | 12/2012 | Woehr et al. |
| 8,377,040 B2 | 2/2013 | Burkholz et al. |
| 8,382,721 B2 | 2/2013 | Woehr et al. |
| 8,398,597 B2 | 3/2013 | Brimhall |
| 8,403,886 B2 | 3/2013 | Bialecki et al. |
| 8,454,574 B2 | 6/2013 | Weaver et al. |
| 8,454,579 B2 | 6/2013 | Fangrow |
| 8,460,247 B2 | 6/2013 | Woehr et al. |
| 8,540,728 B2 | 9/2013 | Woehr et al. |
| 8,568,372 B2 | 10/2013 | Woehr et al. |
| 8,585,660 B2 | 11/2013 | Murphy |

(56) References Cited

U.S. PATENT DOCUMENTS

| | | | |
|---|---|---|---|
| 8,591,469 B2 | 11/2013 | Keyser et al. | |
| 8,597,249 B2 | 12/2013 | Woehr et al. | |
| 8,603,009 B2 | 12/2013 | Tan et al. | |
| 8,647,301 B2 | 2/2014 | Bialecki et al. | |
| 8,647,313 B2 | 2/2014 | Woehr et al. | |
| 8,771,230 B2 | 7/2014 | White et al. | |
| 8,784,386 B2 | 7/2014 | Baid | |
| 8,795,198 B2 | 8/2014 | Tan et al. | |
| 8,814,833 B2 | 8/2014 | Farrell et al. | |
| D713,522 S | 9/2014 | Woehr et al. | |
| D713,957 S | 9/2014 | Woehr et al. | |
| 8,827,965 B2 | 9/2014 | Woehr et al. | |
| 8,834,422 B2 | 9/2014 | Walker et al. | |
| 8,845,584 B2 | 9/2014 | Ferguson et al. | |
| 8,882,742 B2 | 11/2014 | Dikeman et al. | |
| 8,936,575 B2 | 1/2015 | Moulton | |
| 9,033,927 B2 | 5/2015 | Maan et al. | |
| 9,095,683 B2 | 8/2015 | Hall et al. | |
| 9,149,626 B2 | 10/2015 | Woehr et al. | |
| 9,174,036 B2 | 11/2015 | Okamura et al. | |
| 9,180,277 B2 | 11/2015 | Erskine | |
| 9,186,455 B2 | 11/2015 | Moyer | |
| 9,278,195 B2 | 3/2016 | Erskine | |
| 9,289,237 B2 * | 3/2016 | Woehr | A61M 25/0625 |
| 9,314,608 B2 | 4/2016 | Weaver et al. | |
| 9,320,870 B2 | 4/2016 | Woehr | |
| 9,370,641 B2 | 6/2016 | Woehr et al. | |
| 9,402,964 B2 | 8/2016 | Crawford | |
| 9,427,549 B2 | 8/2016 | Woehr et al. | |
| 9,504,786 B2 | 11/2016 | Carlyon et al. | |
| 9,555,220 B2 | 1/2017 | Koehler et al. | |
| 9,555,221 B2 | 1/2017 | Koehler et al. | |
| 9,604,035 B2 | 3/2017 | Keyser et al. | |
| 9,623,210 B2 | 4/2017 | Woehr | |
| 9,764,085 B2 | 9/2017 | Teoh | |
| 9,775,972 B2 | 10/2017 | Christensen et al. | |
| 9,775,973 B2 | 10/2017 | Keyser et al. | |
| 9,782,546 B2 | 10/2017 | Woehr | |
| 9,827,398 B2 | 11/2017 | White et al. | |
| 9,844,646 B2 | 12/2017 | Knutsson | |
| 9,844,648 B2 | 12/2017 | Nakajima et al. | |
| 9,933,079 B2 | 4/2018 | Weaver et al. | |
| 9,962,525 B2 | 5/2018 | Woehr | |
| 10,028,691 B2 | 7/2018 | Goral et al. | |
| 10,052,474 B2 | 8/2018 | Keyser et al. | |
| 10,080,869 B2 | 9/2018 | Woehr et al. | |
| 10,307,571 B2 | 6/2019 | Burkholz | |
| 10,314,984 B2 | 6/2019 | Koehler et al. | |
| 10,406,327 B2 | 9/2019 | Holm et al. | |
| 10,449,331 B2 | 10/2019 | Lim et al. | |
| 10,456,572 B2 | 10/2019 | Woehr | |
| 10,500,375 B2 | 12/2019 | Isaacson et al. | |
| 10,500,376 B2 | 12/2019 | Isaacson et al. | |
| 10,548,522 B2 | 2/2020 | Akcay et al. | |
| 10,589,081 B2 | 3/2020 | Servin De La Mora Godinez et al. | |
| 10,596,351 B2 | 3/2020 | Liska | |
| 10,625,067 B2 | 4/2020 | Al-Ali | |
| 10,661,058 B2 | 5/2020 | Woehr | |
| 10,675,440 B2 | 6/2020 | Abitabilo et al. | |
| 10,682,499 B2 | 6/2020 | Isaacson et al. | |
| 10,695,551 B2 | 6/2020 | Shevgoor et al. | |
| 10,835,729 B2 | 11/2020 | Agrawal et al. | |
| 10,850,068 B2 | 12/2020 | Teoh | |
| 11,071,849 B2 | 7/2021 | Ng et al. | |
| 2002/0161386 A1 | 10/2002 | Halseth et al. | |
| 2002/0165497 A1 | 11/2002 | Greene | |
| 2002/0169418 A1 | 11/2002 | Menzi et al. | |
| 2003/0060760 A1 | 3/2003 | Botich et al. | |
| 2003/0083620 A1 | 5/2003 | Luther et al. | |
| 2003/0100868 A1 | 5/2003 | Ferguson et al. | |
| 2003/0199827 A1 | 10/2003 | Thorne | |
| 2004/0049155 A1 | 3/2004 | Schramm | |
| 2004/0059296 A1 | 3/2004 | Godfrey | |
| 2004/0078003 A1 | 4/2004 | Smith et al. | |
| 2004/0127854 A1 | 7/2004 | Leinsing et al. | |
| 2004/0158208 A1 | 8/2004 | Hiejima | |
| 2004/0168690 A1 | 9/2004 | Payne | |
| 2004/0186434 A1 | 9/2004 | Harding et al. | |
| 2004/0204681 A1 | 10/2004 | Thoresen et al. | |
| 2004/0236288 A1 | 11/2004 | Howell et al. | |
| 2004/0267204 A1 | 12/2004 | Brustowicz | |
| 2005/0038384 A1 | 2/2005 | Li | |
| 2005/0096592 A1 | 5/2005 | Carlyon et al. | |
| 2005/0113755 A1 | 5/2005 | Greene et al. | |
| 2005/0277879 A1 | 12/2005 | Daga | |
| 2006/0036219 A1 | 2/2006 | Alvin | |
| 2006/0041231 A1 | 2/2006 | Pressly et al. | |
| 2006/0229556 A1 | 10/2006 | Pressly et al. | |
| 2007/0191776 A1 | 8/2007 | Bialecki et al. | |
| 2007/0191777 A1 | 8/2007 | King | |
| 2008/0097330 A1 | 4/2008 | King et al. | |
| 2008/0119795 A1 | 5/2008 | Erskine | |
| 2008/0228150 A1 | 9/2008 | Jones et al. | |
| 2009/0137958 A1 | 5/2009 | Erskine | |
| 2009/0209912 A1 | 8/2009 | Keyser et al. | |
| 2009/0222003 A1 | 9/2009 | Otley | |
| 2009/0312711 A1 | 12/2009 | Brimhall | |
| 2010/0042048 A1 | 2/2010 | Christensen | |
| 2010/0241087 A1 | 9/2010 | Moulton | |
| 2011/0015573 A1 | 1/2011 | Maan et al. | |
| 2011/0301551 A1 | 12/2011 | Koehler et al. | |
| 2011/0306933 A1 | 12/2011 | Djordjevic et al. | |
| 2011/0319825 A1 | 12/2011 | Goral et al. | |
| 2012/0035552 A1 | 2/2012 | Woehr | |
| 2012/0089101 A1 | 4/2012 | Carlyon et al. | |
| 2012/0150118 A1 | 6/2012 | Keyser et al. | |
| 2013/0030391 A1 | 1/2013 | Baid | |
| 2013/0165868 A1 | 6/2013 | Isaacson et al. | |
| 2013/0237928 A1 | 9/2013 | Fisher et al. | |
| 2014/0025009 A1 | 1/2014 | Erskine | |
| 2014/0052022 A1 | 2/2014 | Tan et al. | |
| 2014/0058357 A1 | 2/2014 | Keyser et al. | |
| 2014/0200549 A1 | 7/2014 | Norkunas | |
| 2014/0236099 A1 | 8/2014 | Nakagami et al. | |
| 2014/0336582 A1 | 11/2014 | Tisci | |
| 2014/0365809 A1 | 12/2014 | Higeta et al. | |
| 2014/0371715 A1 | 12/2014 | Farrell et al. | |
| 2015/0094751 A1 | 4/2015 | Chen et al. | |
| 2015/0224267 A1 | 8/2015 | Farrell et al. | |
| 2015/0265827 A1 | 9/2015 | Keyser et al. | |
| 2015/0328438 A1 | 11/2015 | Baid | |
| 2016/0008581 A1 | 1/2016 | Ang et al. | |
| 2016/0143616 A1 | 5/2016 | Okubo et al. | |
| 2016/0175563 A1 | 6/2016 | Woehr et al. | |
| 2016/0175576 A1 | 6/2016 | Neff et al. | |
| 2016/0220161 A1 | 8/2016 | Goral et al. | |
| 2016/0220791 A1 | 8/2016 | Akcay et al. | |
| 2016/0271370 A1 | 9/2016 | Keyser et al. | |
| 2016/0331935 A1 | 11/2016 | Saatchi et al. | |
| 2016/0361490 A1 | 12/2016 | Phang et al. | |
| 2016/0361519 A1 | 12/2016 | Teoh et al. | |
| 2016/0374685 A1 | 12/2016 | Abbott et al. | |
| 2017/0035992 A1 | 2/2017 | Harding et al. | |
| 2017/0035995 A1 | 2/2017 | Shevgoor et al. | |
| 2017/0043134 A1 * | 2/2017 | Harding | A61M 5/34 |
| 2017/0120011 A1 | 5/2017 | Burkholz et al. | |
| 2017/0120017 A1 | 5/2017 | Burkholz et al. | |
| 2017/0274183 A1 | 9/2017 | Burkholz et al. | |
| 2017/0319822 A1 | 11/2017 | Ang | |
| 2017/0333642 A1 | 11/2017 | Shevgoor et al. | |
| 2017/0361070 A1 | 12/2017 | Hivert | |
| 2018/0064912 A1 | 3/2018 | Keyser et al. | |
| 2018/0078741 A1 | 3/2018 | Stokes | |
| 2018/0154119 A1 | 6/2018 | White et al. | |
| 2018/0214673 A1 | 8/2018 | Ng et al. | |
| 2018/0214682 A1 * | 8/2018 | Woehr | A61M 25/0606 |
| 2018/0256885 A1 | 9/2018 | Shevgoor et al. | |
| 2018/0289932 A1 | 10/2018 | Isaacson et al. | |
| 2018/0296149 A1 | 10/2018 | Goral et al. | |
| 2018/0304048 A1 | 10/2018 | Knutsson | |
| 2018/0311475 A1 * | 11/2018 | Baid | A61M 5/3273 |
| 2018/0361119 A1 | 12/2018 | Goral et al. | |
| 2019/0160264 A1 * | 5/2019 | Isaacson | A61M 5/3243 |

(56) References Cited

U.S. PATENT DOCUMENTS

| | | | |
|---|---|---|---|
| 2019/0262549 A1 | 8/2019 | Koehler et al. | |
| 2019/0351210 A1 | 11/2019 | Solomon et al. | |
| 2020/0094026 A1 | 3/2020 | Isaacson et al. | |
| 2020/0094037 A1 | 3/2020 | Tran et al. | |
| 2020/0121896 A1 | 4/2020 | Baid | |
| 2020/0146605 A1 | 5/2020 | Paliwoda | |
| 2020/0155808 A1 | 5/2020 | Burkholz et al. | |
| 2020/0188634 A1* | 6/2020 | Woehr | A61M 25/0097 |
| 2020/0197667 A1 | 6/2020 | Gupta | |
| 2020/0261702 A1 | 8/2020 | Jewell et al. | |
| 2021/0187249 A1 | 6/2021 | Lagana' et al. | |
| 2021/0308427 A1 | 10/2021 | Ng et al. | |
| 2021/0370020 A1 | 12/2021 | Gupta | |
| 2021/0402143 A1 | 12/2021 | Yokota et al. | |
| 2022/0355072 A1 | 11/2022 | Gupta et al. | |

FOREIGN PATENT DOCUMENTS

| | | |
|---|---|---|
| CA | 2033361 C | 11/2002 |
| CA | 2710969 A1 | 7/2009 |
| CN | 106659438 A | 5/2017 |
| CN | 107427633 A | 12/2017 |
| DE | 4442352 C1 | 12/1995 |
| EP | 0747083 A2 | 12/1996 |
| EP | 0747085 A2 | 12/1996 |
| EP | 0750916 A2 | 1/1997 |
| EP | 3209363 B1 | 3/2019 |
| EP | 3622992 A1 | 3/2020 |
| EP | 3622999 A1 | 3/2020 |
| IN | 201911036272 | 1/2020 |
| JP | 07024071 A | 1/1995 |
| JP | 2001046507 A | 2/2001 |
| JP | 2001190683 A | 7/2001 |
| JP | 20041544364 A | 6/2004 |
| JP | 2022551563 A | 12/2022 |
| WO | 9308865 A1 | 5/1993 |
| WO | 9413341 A1 | 6/1994 |
| WO | 0168174 A2 | 9/2001 |
| WO | 2007061718 A2 | 5/2007 |
| WO | 2007098355 A1 | 8/2007 |
| WO | 2010107645 A1 | 9/2010 |
| WO | 2011152916 A1 | 12/2011 |
| WO | 2013051242 A1 | 4/2013 |
| WO | 2015161294 A1 | 10/2015 |
| WO | 2016033143 A1 | 3/2016 |
| WO | 2016063287 A1 | 4/2016 |
| WO | 2016135293 A2 | 9/2016 |
| WO | 2017042825 A2 | 3/2017 |
| WO | 2018096549 A1 | 5/2018 |
| WO | 2018217781 A1 | 11/2018 |
| WO | 2019008432 A1 | 1/2019 |
| WO | 2019152630 A1 | 8/2019 |
| WO | 2020011663 A1 | 1/2020 |
| WO | 2020120404 A1 | 6/2020 |
| WO | 2020189466 A1 | 9/2020 |
| WO | 2021048867 A1 | 3/2021 |
| WO | 2022235744 A1 | 11/2022 |
| WO | 2023137377 A1 | 7/2023 |
| WO | 2023137380 A1 | 7/2023 |

OTHER PUBLICATIONS

International Preliminary Report on Patentability issued in International Application No. PCT/US2022/016002, mailed on Aug. 24, 2023, 6 pages.

"PTFE—Polytetrafluoroethylene", Summary of Properties, Jul. 4, 2017, Zeus Inc.

International Search Report and Written Opinion dated Jul. 20, 2022 in connection with International Patent Application No. PCT/US2022/027597, 9 pages.

International Search Report and Written Opinion for PCT Application No. PCT/IN2018/050178, Dated Jun. 12, 2018, 8 pages.

International Search Report and Written Opinion dated Apr. 19, 2022 in connection with International Patent Application No. PCT/US2022/016002, 7 pages.

International Search Report and Written Opinion issued in International Application No. PCT/US2023/060554, mailed on May 9, 2023, 11 pages.

First Examination Report issued in Indian Patent Application No. 201911036272, mailed on Feb. 10, 2020, 5 pages.

Hearing Notice issued in Indian Patent Application No. 201911036272, mailed on Jul. 16, 2020, 2 pages.

International Preliminary Report on Patentability issued in International Application No. PCT/US2023/060554, mailed on Jul. 25, 2024, 10 pages.

International Preliminary Report on Patentability issued in International Patent Application No. PCT/US2023/060560, mailed on Jul. 25, 2024, 9 pages.

Extended European Search Report issued in European Patent Application No. 22799471.2, mailed on Feb. 13, 2025, 11 pages.

Office Action issued in Canadian Patent Application No. 3,169,051, mailed on Feb. 12, 2025, 4 pages.

Murty , "Use of Stainless Steels in Medical Applications", Medical Device Materials: Proceedings of the Material & Processes for Medical Devices Conference, pp. 288, 2003.

Extended European search report issued in European Application No. 23740832.3, mailed on Dec. 2, 2025, 15 pages.

Partial European Search Report issued in European Patent Application No. 23740835.6, mailed on Dec. 1, 2025, 15 pages.

* cited by examiner

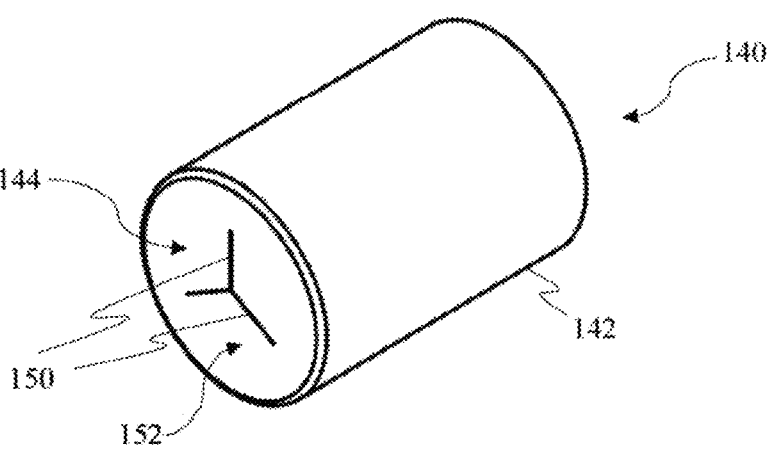
FIG. 5A
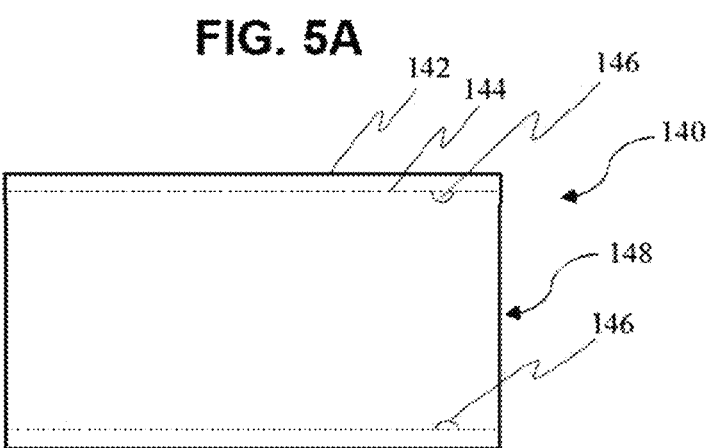
FIG. 5B
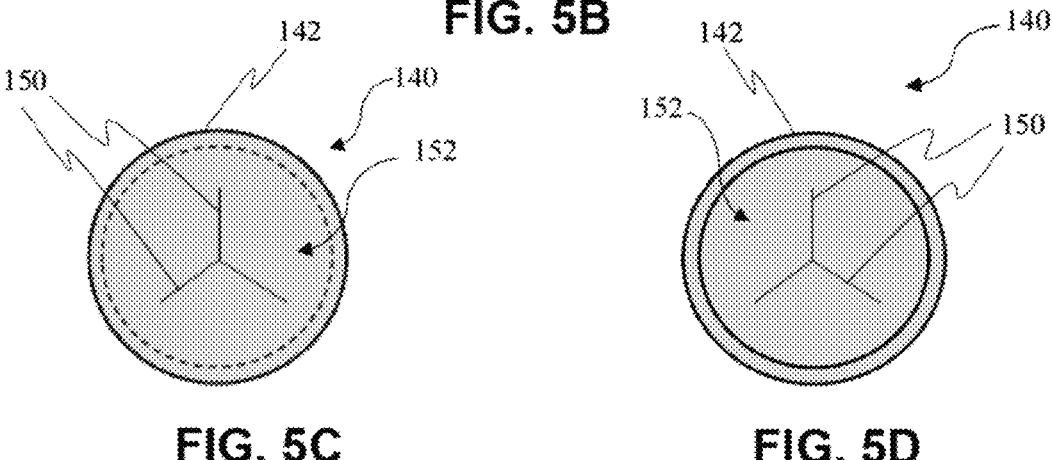
FIG. 5C                    FIG. 5D

FIG. 7A                    FIG. 7B

INTRAVENOUS CANNULA

CROSS-REFERENCE TO RELATED APPLICATION

This patent application claims the priority of Indian patent application number 202111005687, filed Feb. 10, 2021 entitled "Intravenous Cannula," the disclosure content of which is hereby incorporated by reference.

TECHNICAL FIELD

The present disclosure relates to medical devices. More particularly, the disclosure relates to intravenous cannulas configured to prevent backflow of blood and needle prick injuries.

BACKGROUND OF THE DISCLOSURE

Intravenous (IV) cannulas have been in existence for many years. Intravenous cannulas are venous devices used to infuse medication or fluids directly into a vein or draw blood samples for testing. Intravenous cannulas are introduced into a vein using a needle and fixed to the patient's skin with an adhesive tape.

One drawback associated with the use of over-needle intravenous cannulas is that once the needle is withdrawn from the cannula, there is an open channel for the blood to flow through the cannula and spill out of a catheter hub. The blood may be contaminated and this may lead to risk of infection for the healthcare worker. Additionally, spillage of blood leads to unhygienic conditions for the patient as well as in the healthcare space where the catheter is applied. Blood spillage is currently a major problem during administration of IV catheters. Additionally, over-needle cannulas that provide protection to a user from a "needle stick" or "needle prick" injuries is not yet prevalent. The risks associated with such "needle prick" injuries are high because of the high prevalence of communicable diseases among patients in hospitals and especially in emergency rooms where cannulation treatment must be initiated immediately. Also, the costs associated with any complication or adverse effects associated with such "needle prick" injuries are very high.

There are known methods to avoid blood spillage, however these methods are associated with certain risks and drawbacks. One such method is to apply a manual pressure to the vein before withdrawal of the needle to stop the flow of blood, but this method requires either a two-hand technique achieved by operators of considerable skill, or two operators may even be required. In either case, the flow of blood still cannot be stopped. In another known device, a closed system intravenous cannula is used in which the flow of blood is stopped by having a dead stopper in the path of the blood flow, and a side port is provided at an angle to the catheter to allow air escape for flashback visualization and to allow infusion of fluid. However, these products are bulky, complicated to use, and more expensive. In yet another known method, the catheter space may be blocked by a mandrel or obturator which requires proper skill and training and that further makes the product complicated in structure and to operate, and is expensive.

Similarly, there are known methods for avoiding "needle prick" injuries, wherein conventional catheter introducer devices are employed. However, these catheter introducer devices require additional training for the user to operate. Also, the needle catheter assembly is not robust, as the user remains in contact with the needle tip cover and in case the needle cover tip is manipulated by the user during application, the user may get exposed to the needle tip and thus the risk of injuries to the user while operating the catheter introducer assembly is high. Also, manufacturing of such needle catheter assemblies is complex and not cost effective.

Indian Patent application number 3031/DEL/2014, (hereafter referred to as Pat '3031) provides a catheter device. One of the problems associated with the device disclosed in Pat '3031 is that when the needle is retracted from the needle cover, the needle cover does not disengage from the catheter hub, and more force is required to disengage the needle cover from the catheter hub. Another problem associated with the needle disclosed in Pat '3031 is that the needle does not engage the needle cover with the catheter hub, which affects the functionality of the catheter. This may lead to manipulation of the catheter device by the operator to extract the needle cover from the hub, which in turn may disturb and damage the vein, thereby causing pain to the patient.

In addition to the above limitations and associated problems, the existing devices having leaf springs, for example as disclosed in Pat '3031, face problems related to improper guiding of the needle tip inside the catheter hub when the needle is inserted through the leaf spring.

This may lead to blunting of needle tip when the needle tip contacts the other parts of the safety pin or the catheter hub when operated to move into the catheter hub.

In light of the foregoing discussion, there is a need for an intravenous cannula that can overcome the limitations stated above in addition to providing other technical advantages.

SUMMARY OF THE DISCLOSURE

Embodiments of the present disclosure disclose an intravenous cannula. The cannula includes a catheter hub having a proximal end, a distal end and a first chamber. An actuator member is disposed within the first chamber and has an axial bore. The actuator member is adapted to be axially displaced towards the distal end of the catheter hub to form a passage for fluid flow from the proximal end of the catheter hub to the distal end of the catheter hub, when a luer lock member removably connected to the proximal end of the catheter hub displaces the actuator member. A tubular valve member is disposed within the first chamber and adapted to allow a needle member to pass through. The tubular valve member is defined with a flat portion at a first end, the flat portion configured with one or more slits defining a plurality of prongs. The slits are configured to allow the needle member to pass through for puncturing a vein of a subject. The prongs are displaced by the actuator member for fluid flow from the proximal end of the catheter hub to the distal end of the catheter hub, when the luer lock member displaces the actuator member.

Further, a valve closure member is provided in the cannula. The valve closure member comprises a first surface at a proximal end, a second surface at a distal end, and a through-hole. The valve closure member is disposed in the catheter hub such that the first surface abuts an undercut portion defined in the catheter hub, and the second surface abuts the flat portion of the tubular valve member. The valve closure member is adapted to displace the prongs to close the passage for fluid flow and prevent blood flow from the punctured vein of the subject from the distal end of the catheter hub to the proximal end of the catheter hub, when the luer lock member abutting the actuator member is removed.

Additionally, a needle guard assembly is provided in the cannula. The needle guard assembly includes a body portion connected to the proximal end of the catheter hub. A safety clip biasing outwardly locks onto at least one interlocking flange defined in the body portion. The safety clip in a biased condition allows the needle member to extend through the body portion and the catheter hub. Upon withdrawal of the needle member from the proximal end of the catheter hub, the safety pin disengages from the interlocking flange and arrests a tip portion of the needle member within the safety clip, thereby preventing needle prick injury upon withdrawal of the needle member from the catheter hub.

In an embodiment, the safety clip consists of a bracket defining an opening for receiving the needle member, the bracket adapted to be disposed within the body portion. A first resilient arm extends from one end of the bracket and has a connecting portion for engaging with the at least one interlocking flange of the body portion and the needle member. The first resilient arm has a first section and a second section, such that dimensions of the first section are larger than the second section. Further, a second resilient arm extends from an opposing end of the bracket and has a connecting portion for engaging with the at least one interlocking flange of the body portion and the needle member. The second resilient arm has a first section and a second section, such that dimensions of the first section are larger than the second section. The connecting portion of each of the first and second resilient arms is adapted to engage with the interlocking flange and a body of the needle member, when the needle member is extending through the catheter hub for puncturing the vein of the subject and to disengage from the interlocking flange and the body of the needle member when the needle member is withdrawn from the proximal end of the catheter hub.

In an embodiment, the connecting portion of each of the first and second resilient arms includes a curved protrusion at a fore end, adapted to engage with the at least one interlocking flange of the body portion and a curved lip. The curved lip extends inwardly towards the bracket member at an aft end and is adapted to engage on to the needle member. The curved lip is adapted to arrest the tip portion of the needle member within the safety clip, when the needle member is withdrawn from the proximal end of the catheter hub.

In an embodiment, the curved protrusion includes a projection extending towards the bracket. The projection along with the second section of the first and second resilient arms define a seat portion. The seat portion is adapted to receive and seat the tip portion of the needle member, thereby preventing misalignment of the needle member during withdrawal from catheter hub.

In an embodiment, the length of the first resilient arm is greater than the length of the second resilient arm.

In an embodiment, at least one of the bracket, the first resilient arm and the second resilient arm is defined with at least one rib member, for reinforcement.

In an embodiment, the rib member is provided at a second section of the first and the second resilient arms, as reinforcement to the first and the second resilient arms.

In an embodiment, each of the at least one interlocking flange of the body portion extends radially inwardly for ensuring engagement with the safety clip in its biased condition, so that the safety clip is retained within the needle guard assembly.

In an embodiment, the needle member is configured with a protuberance defined proximal to its distal end. The protuberance is adapted to engage with the bracket during withdrawal of the needle member from the proximal end of the catheter tube, thereby preventing retrieval of the needle member from the needle guard assembly.

In an embodiment, the first surface of the valve closure member is concave or frusto-conical in shape.

BRIEF DESCRIPTION OF ACCOMPANYING DRAWINGS

The above and other features, aspects, and advantages of the subject matter will be better understood with regard to the following description and accompanying drawings:

FIG. 5A is a perspective view of a tubular valve member of the cannula, according to an exemplary embodiment of the present disclosure;

FIG. 5B is a sectional view of the tubular valve member of FIG. 5A, according to an exemplary embodiment of the present disclosure;

FIG. 5C is a front view of the tubular valve member of FIG. 5A, according to an exemplary embodiment of the present disclosure;

FIG. 5D is a rear view of the tubular valve member of FIG. 5A, according to an exemplary embodiment of the present disclosure;

FIG. 7A is a perspective view of a valve closure member of the cannula, according to an exemplary embodiment of the present disclosure;

FIG. 7B is a sectional view of the valve closure member of FIG. 7A, according to an exemplary embodiment of the present disclosure;

DETAILED DESCRIPTION OF THE DISCLOSURE

Provided below is a non-limiting exemplary embodiment of the present invention. Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claim(s).

Figure 1:
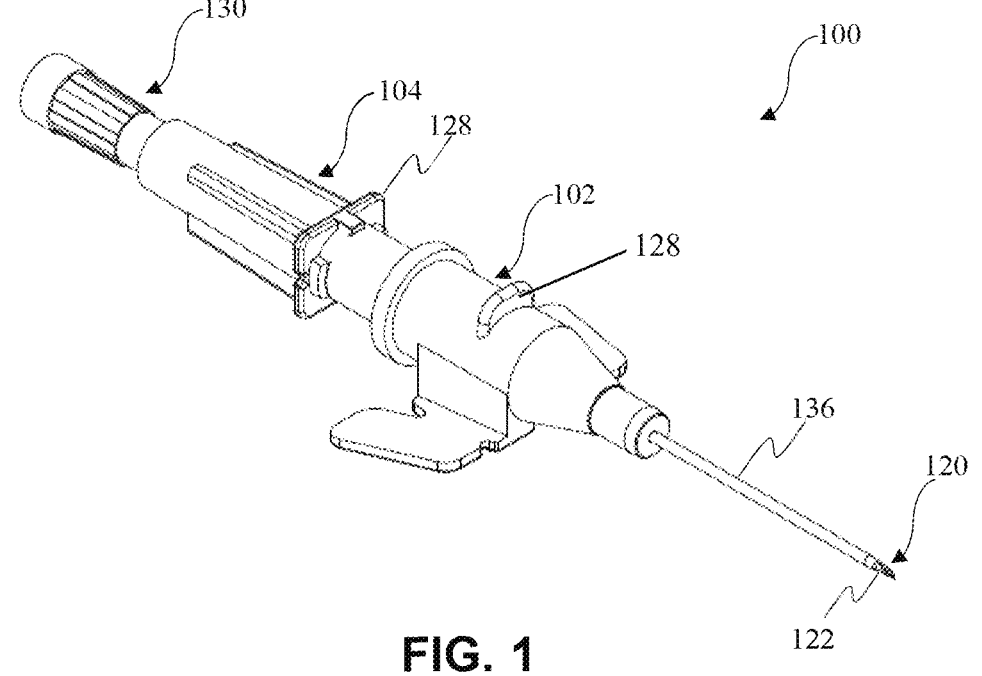
FIG. 1 is a perspective view of an intravenous cannula, according to an exemplary embodiment of the present disclosure.
Figure 2:
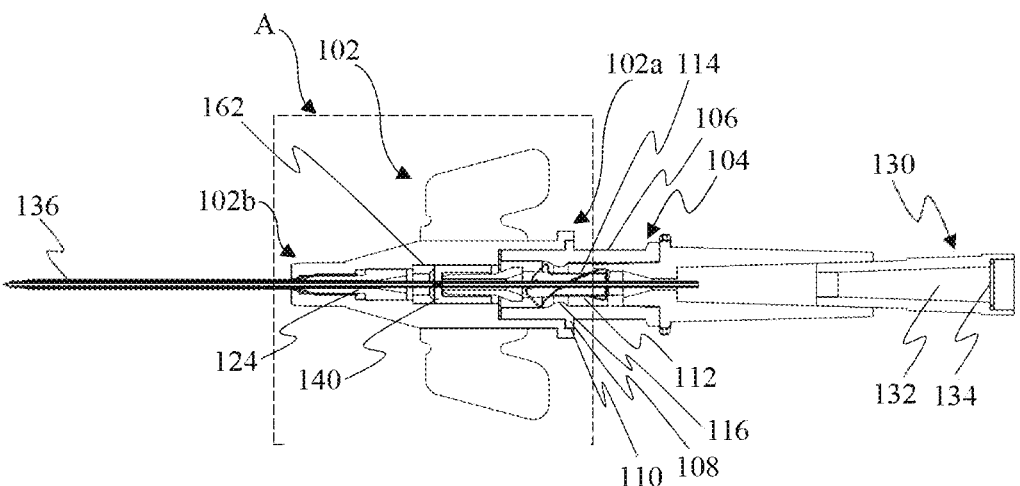
FIG. 2 is a sectional view of the intravenous cannula shown in FIG. 1.

FIGS. 1 and 2 are perspective and sectional views of a cannula (100) according to an exemplary embodiment of the present disclosure. The cannula (100) is a medical device used onto a subject [not shown in FIGS.] who may be a user, undergoing a treatment for administration of a medication fluid by an intravenous therapy. The cannula (100) may also be used to carry out other tasks based on type of cannula. In the illustrated FIGS., the cannula (100) is an intravenous cannula (100). The term 'intravenous cannula (100)' as referred to in the present disclosure will be used interchangeably with 'cannula (100)' for brevity. The illustrated intravenous cannula (100) includes a catheter hub (102) (more clearly shown in FIG. 3, which illustrates a magnified view of the catheter hub (102) and it has been indicated by portion "A" in FIG. 2).

The cannula (100) further includes a needle guard assembly (104) having a body portion (106) connected to the catheter hub (102) such that a projection (108) on the body portion (106) engages with a recess (110) in the catheter hub (102). The body portion (106) includes a bore (112) configured for receiving a safety clip (114), which will be described in detail in the description pertaining to FIG. 8. The safety clip (114) is disposed within the body portion (106) such that the safety clip (114) engages onto at least one interlocking flange (116) defined in the body portion. The safety clip (114) in a biased condition (118) [as shown in FIG. 9A] allows a needle member (120) to extend through the body portion (106) and the catheter hub (102). Upon withdrawal of the needle member (120) from the proximal end (102a) of the catheter hub (102), the safety pin (114) disengages from the interlocking flange (116) to arrest a tip portion (122) of the needle member (120) in the catheter hub (102) and prevent a forward movement of the needle member (120) and retain the tip portion (122) within the safety clip (114), thereby preventing needle prick injury to the user during withdrawal of the needle member (120).

The body portion (106) further includes a tubular sleeve (124) that extends axially from the catheter hub (102) up to a needle hub (126), connected to the body portion (106). The needle hub (126) is fixedly connected to the needle member (120) and is in a tight-fit relationship with the body portion (106). As such, when the needle member (120) is withdrawn from the catheter hub (102), the needle hub (126) disengages from the body portion (106). Also, due to the construction of the safety clip (114) within the body portion (106), the safety clip (114) also disengages from the body portion (106) and is withdrawn along with the needle member (120). As such, the tip portion (122) of the needle member (120) is not exposed to the user during withdrawal of the needle member (120), and hence needle prick injury to the user is prevented. In an embodiment, the needle hub (126) may be provided with a thumb grip 128 for enabling a user to grip the cannula (100) for insertion and/or retraction of the cannula (100).

Further, the needle hub (126) is releasably connected to a flow control hub (130) through an extended portion of the needle hub (126) and can be closed using a threaded cap or a luer lock cap at one end. The flow control hub (130) may include a flashback chamber (132), wherein blood flow into the flashback chamber (132) confirms puncturing of the vein by the needle member (120). The flashback chamber (132) may include a porous filter (134) [as shown in FIG. 2] and a cover [not shown] to allow air to escape and blood to flow inside the flashback chamber (132). The flashback chamber (132) may additionally include a hydrophobic filter for preventing spillage of blood from the flashback chamber (132).

Figure 3:
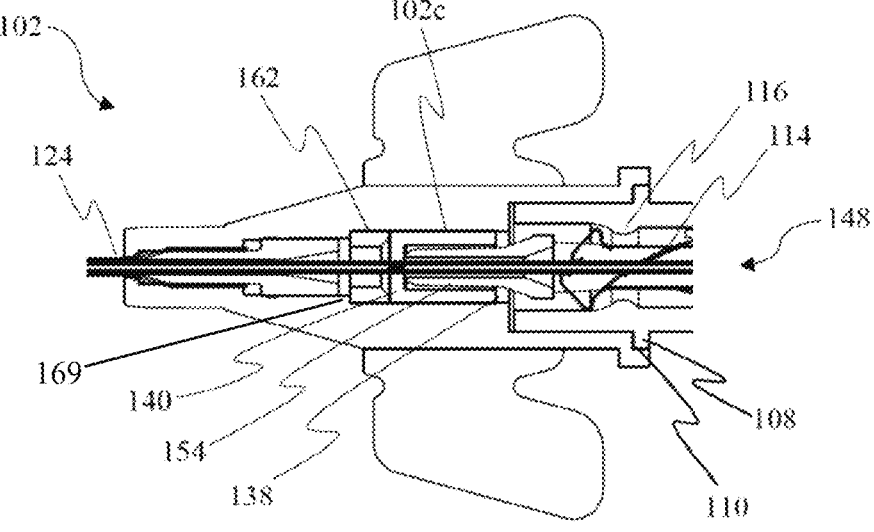
FIG. 3 is a magnified view of portion "A" depicting a catheter hub of the intravenous cannula of FIG. 2.
Figure 4:
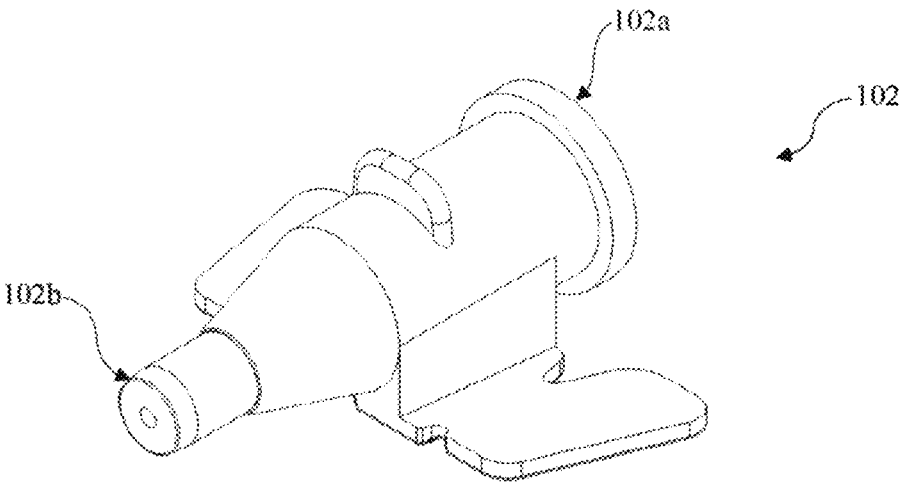
FIG. 4 is a perspective view of the catheter hub shown in FIGS. 1-3.

Referring to FIG. 4 in conjunction with FIGS. 1-3, the catheter hub (102) includes a proximal end (102a) and a distal end (102b). It is to be understood that the term 'proximal end' as used in the present disclosure may be defined as an end closer to the operator or user who operates the cannula (100). The term 'distal end' as used in the present disclosure may be defined as an end opposite to the 'proximal end' and away from the operator or user. In an embodiment, the catheter hub (102) can be made of a bio-compatible material which can be rigid and can securely hold components associated with it. The catheter hub (102) includes a catheter tube (136) (shown in FIGS. 1 and 2) fixedly connected at the distal end (102b) of the catheter hub (102). The catheter tube (136) can be made of a flexible or a soft material including, but not limited to, a plastic or a polymer or a bio-compatible material which is flexible/soft in nature. The catheter tube (136) is a thin elongated tubular structure having a first chamber (102c). The bore of the catheter tube (136) is adapted to encase the needle of the intravenous cannula (100). The catheter tube (136) can be adapted to fix with the catheter hub (102) by a method including but not limited to, a press fitting or adhesive bonding or any other methods known in the art to serve a purpose of holding the catheter tube (136) with the catheter hub (102). The catheter tube (136) may be manufactured integrally with the catheter hub (102).

In an embodiment, the catheter hub (102) may also include an outer port [not shown] abutting on an outer surface of the catheter hub (102) forming an auxiliary fluid pathway in communication with a co-axial recess (148) of the catheter hub (102). Thus, the intravenous cannula (100) may also be adapted to have a two-way fluid mechanism. Accordingly, the catheter hub (102) may be provided with a dispensing cap [not shown] for opening and closing of the outer port for supply of a fluid.

The catheter hub (102) further includes an annular stopper (138) on an inner surface of the catheter hub (102). The annular stopper (138) is disposed at the proximal end of the catheter hub (102). In an embodiment, the luer lock cap is provided to seal the proximal end of the catheter hub (102). The catheter hub (102) is adapted to accommodate a tubular valve member (140) of the cannula (100).

Referring now to FIGS. 5A-5D in conjunction with FIGS. 1-4, the tubular valve member (140) is adapted to be disposed within the co-axial recess (148) of the catheter hub (102). The tubular valve member (140) is defined by a cylindrical portion (142) having a protrusion (146) (shown in FIG. 5B) at an inner surface. The tubular valve member (140) further includes a co-axial recess (148) (shown in FIG. 5B). The tubular valve member (140) includes a flat portion (144) which is provided with one or more slits (150), thereby defining a plurality of prongs (152). The one or more slits (150) are designed to allow the needle member (120) to pass through the slits (150) so that the slits (150) can self-seal once the needle is withdrawn.

Further, the tubular valve member (140) is adapted to be held in place at the co-axial recess (148) of the catheter hub (102) when a first end of the tubular valve member (140) abuts the annular stopper (138) of the catheter hub (102). In an embodiment, the tubular valve member (140) is made of a flexible material selected from a group consisting of silicone and rubber, where the slit is of shape such as, but not limited to, 'Y' or inverted 'Y' or 'X', or a horizontal slit or a vertical slit or '+' shape or combination of the same or any other shape which will facilitate opening and expanding of the plurality of prongs (152) during the insertion of the needle and an actuator member (154) respectively, inside the co-axial recess (148) of the tubular valve member.

Figure 6:
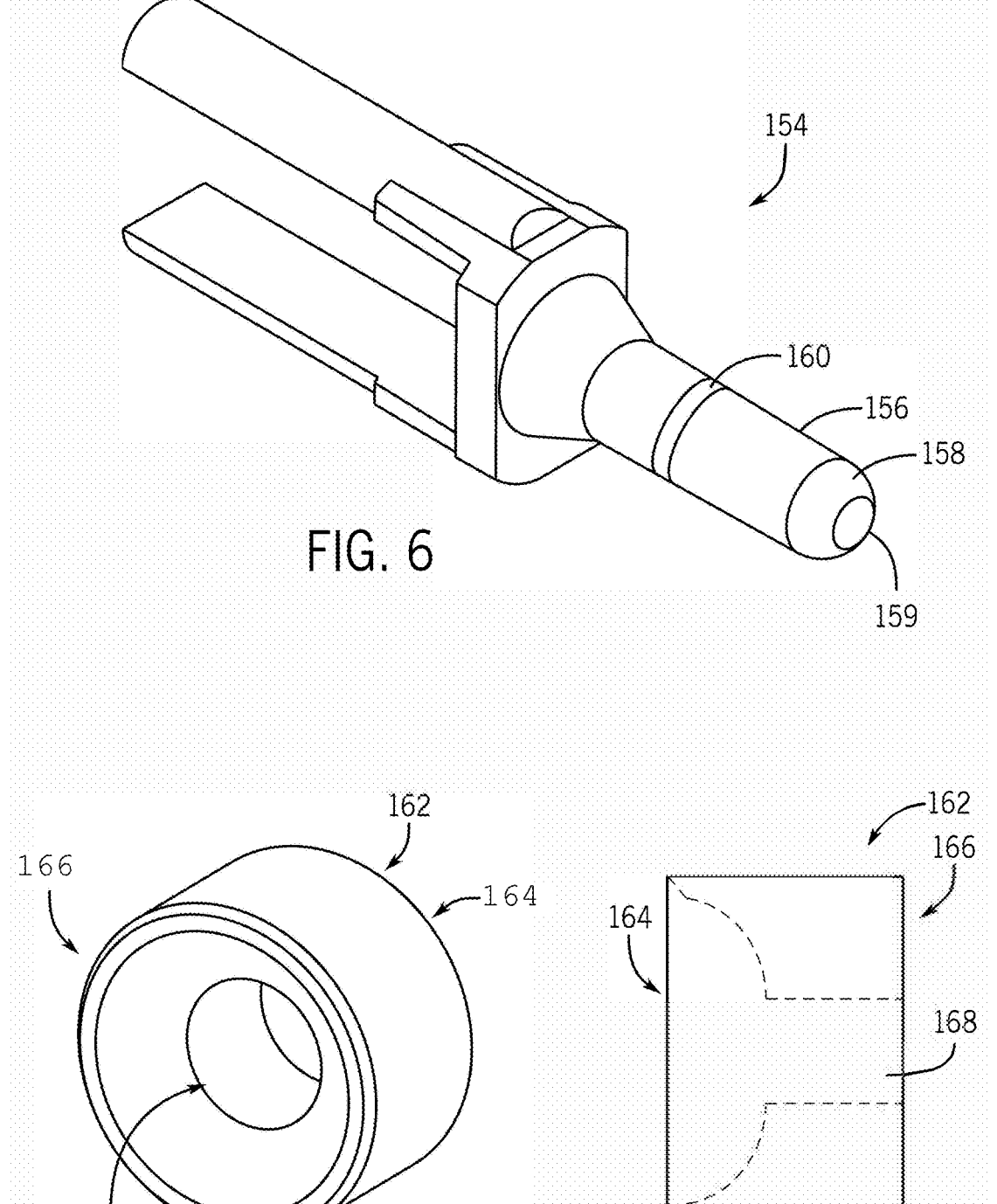
FIG. 6 is a perspective view of an actuator member of the cannula, according to an exemplary embodiment of the present disclosure.

FIG. 6 is a perspective view of the actuator member (154) positioned within the cannula (100), in accordance with an exemplary embodiment of the present disclosure. The actuator member (154) includes a first end having a radially extending flange (156), a second end having a convex surface (158) and an axial bore (159) between the first end and the second end of the actuator member (154). In an embodiment, the actuator member (154) is made of medical grade materials known in the art, such as, but not limited to, a rigid plastic material for example Polyoxymethylene (POM) or a metal for example Stainless Steel.

The actuator member (154) further includes a circular recess (160) on an outer surface, such that the protrusion (146) of the tubular valve member (140) is adapted to engage with the circular recess (160). The engagement of the protrusion (146) and the circular recess (160) of the actuator member (154) ensures rigid construction, and thus assembly of the tubular valve member (140) and the actuator member (154) does not fall from the catheter hub (102).

In an embodiment, the tubular valve member (140) and the actuator member (154) may be connected by any other methods apart from the protrusion (146) and the recess, for example threads (not shown), or snap fit arrangement (not shown) etc., known in the art. In yet another embodiment, the actuator member (154) can include a protrusion (146) similar to that of the protrusion (146) made on the tubular valve member (140), and the tubular valve member (140) may include a circular recess (160) similar to that of the circular recess (160) of the actuator member (154). It should be understood that the circular recess (160) and the protrusion (146) made on the actuator member (154) and the valve member (140) should not be limiting to the scope of the present disclosure, and any suitable mechanism (for example: threads) which serves the purpose of assembling the actuator member (154) and the valve member (140) may be employed.

FIGS. 7 A and 7B illustrate perspective and schematic views of a valve closure member (162) of the intravenous cannula (100), according to an exemplary embodiment of the present disclosure. The valve closure member (162) includes a first surface (164) at a proximal end, a second surface (166) at a distal end, and a through-hole (168) extending between the proximal end and the distal end. The valve closure member (162) is disposed inside the catheter hub (102) such that the second surface (166) of the valve closure member (162) abuts the undercut portion (169) of the catheter hub (102) and the first surface (164) of the valve closure member (162) abuts the flat portion (144) of the valve member (140). In an embodiment, the valve closure member (162) may have a hardness ranging from about 50 shore to about 80 shore and the valve member (140) may have a hardness ranging from about 20 shore to about 45 shore.

Figure 8:
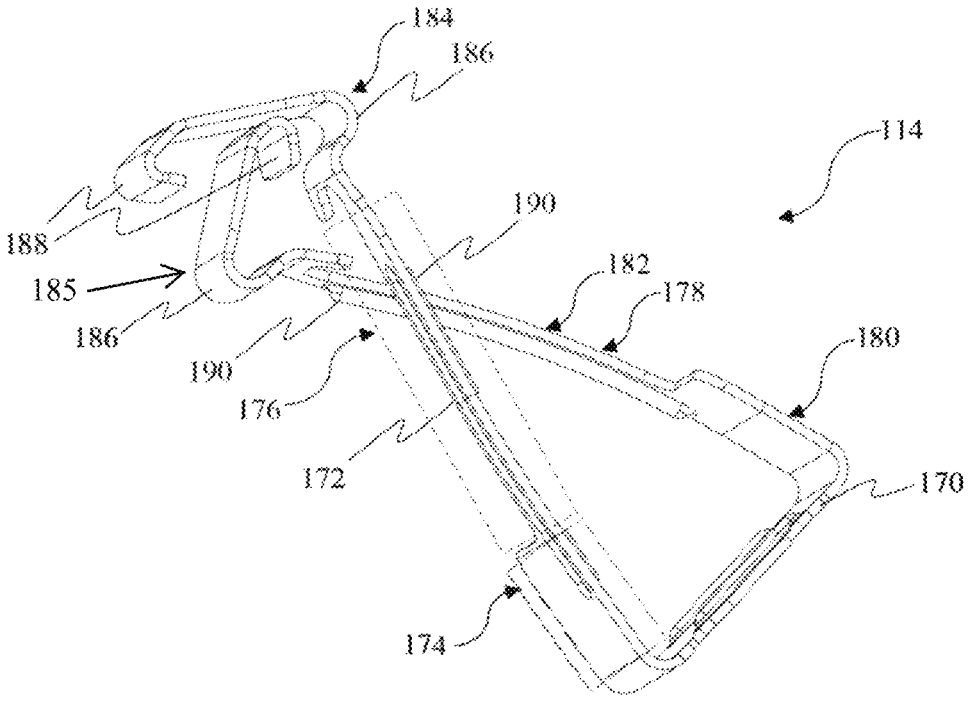
FIG. 8 is a perspective view of a safety clip disposed within a needle guard assembly of the cannula, according to an exemplary embodiment of the present disclosure.
Figure 9A:
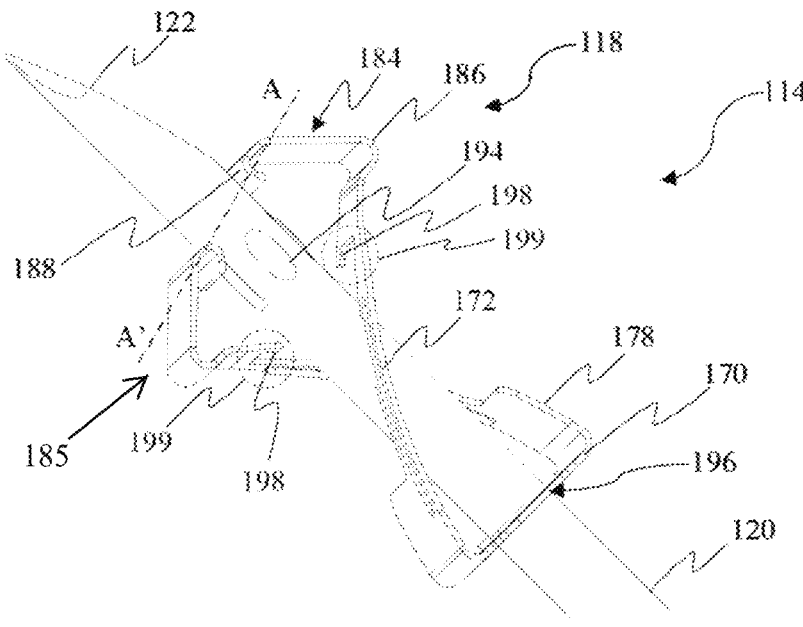
FIG. 9A is a perspective view of the safety clip in a biased condition due to a needle member inserted within the catheter hub, according to an exemplary embodiment of the present disclosure.
Figure 9B:
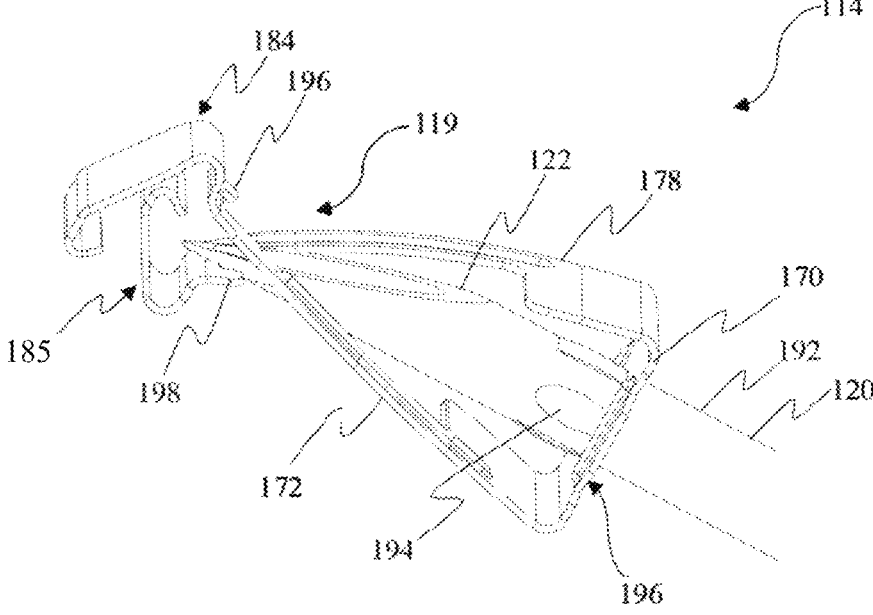
FIG. 9B is a perspective view of the safety clip in an unbiased condition due to the needle member being withdrawn from the catheter hub, according to an exemplary embodiment of the present disclosure.

Referring now to FIGS. 8, 9A, and 9B in conjunction with FIG. 2, the safety clip (114) disposed within the needle guard assembly (104) is illustrated. The safety clip (114) is configured to block entry of the needle member (120) into the catheter hub (102) and retain the tip portion (122) of the needle member (120) therein, when the needle member (120) is withdrawn from the catheter hub (102). The safety clip (114) includes a bracket (170) defining an opening (196) for receiving the needle member (120). The opening (196) may be configured based on the diameter of the needle member (120) to be employed in the cannula (100).

A first resilient arm (172) extends from one end of the bracket (170) and has a first section (174) and a second section (176) such that, dimensions of the first section (174) are larger than the second section (176). As an example, the first section (174) may be wider than the second section (176). Such a construction of the safety clip (114) renders effortless and inexpensive manufacturing of the safety clip (114), while ensuring sufficient spring force or biasing force requirements. The first section (174) may further conform to the dimensions of the bracket (170) and thus ensure uniformity in construction, retaining structural rigidity of the safety clip (114) when subjected to deformation.

A second resilient arm (178) extends from another end of the bracket (170) and has a first section (180) and a second section (182) such that, dimensions of the first section (180) are larger than the second section (182). As an example, the first section (180) may be wider than the second section (182). Such a construction of the safety clip (114) renders effortless and inexpensive manufacturing of the safety clip (114), while ensuring sufficient spring force or biasing force requirements. The first section (180) may further conform to the dimensions of the bracket (170) and thus ensure uniformity in construction, retaining structural rigidity of the safety clip (114) when subjected to deformation.

Further, a connecting portion (each of 184 and 185) is provided to each of the first and second resilient arms (172, 178), preferably at the second section (182). [The] Each connecting portion (184, 185) is adapted to engage with at least one interlocking flange (116) configured on an inner surface of the body portion (106) and the needle member (120). Each connecting portion (184, 185) is adapted to engage with the interlocking flange (116) and a body (192) of the needle member (120), when the needle member (120) is extending through the catheter hub (102) for puncturing the vein of the subject. Each connecting portion (184, 185) further disengages from the interlocking flange (116) and the body (192) of the needle member (120), when the needle member (120) is withdrawn from the proximal end (120a) of the catheter hub (102).

As depicted in FIG. 8, each connecting portion (184, 185) includes a curved protrusion (186) at a fore end and a curved lip (188) at an aft end. The curved protrusion (186) is adapted to engage with the interlocking flange (116) of the body portion (106), so that the safety clip (114) is held within the body portion (106). The curved lip (188) provided at the aft end extends inwardly towards the bracket (170) and is adapted to engage the needle member (120).

The curved protrusion (186) engages with the interlocking flange (116) due to biasing of the first and the second resilient arms (172, 178). The first and the second resilient arms (172, 178) are biased or flexed due to insertion of the needle member (120) into the catheter hub (102) [more clearly shown in FIGS. 2 and 9A]. In other words, insertion or presence of the needle member (120) in the needle guard assembly (104) urges the first and the second resilient arms (172, 178) to flex away from each other, thereby engaging the curved protrusion (186) to engage with the interlocking flange (116). At the same time, the curved lip (188) engages with the body (192) of the needle member (120), so that the biasing force is maintained and hence ensuring that the safety clip (114) is retained within the body portion (106).

In an exemplary embodiment, the curved protrusions (186) of the first and the second arms (172, 178) are outwardly extending protrusions that are configured for engaging the interlocking flanges (116) in the body portion (106), which are inwardly protruding. Accordingly, the construction or shape or configuration of the curved protrusion (186) may be selected based on the construction of the interlocking flanges (116), so that interlocking therebetween is ensured when the needle member (120) is present in the catheter hub (102).

In another embodiment, the curved lip (188) of the first and the second arms (172, 178) may be inwardly extending protrusions that are configured for engaging with the needle member (120) when the needle member (120) is present within the catheter hub (102) and arresting the tip portion (122) of the needle member (120) within the safety clip (114) when the needle member (120) is withdrawn from the catheter hub (102). As such, the curved lip (188) is adapted to prevent "entry or re-entry" of the needle member (120) beyond the safety clip (114), when the needle member (120) is withdrawn from the catheter hub (102). Accordingly, the construction or shape or configuration of the curved lip (188) may be selected based on the configuration of the needle member (120) or the position at which the needle member (120) is inserted or withdrawn. As an example, the curved protrusion (186) may be an inverted U-shaped member, while the curved lip (188) may be a U-shaped member.

Further, the curved protrusion (186) on each of the first and the second arms (172, 178), includes a projection (198) extending towards the bracket (170). The projection (198) along with the second section (176) of the respective arms define a seat portion (199). The seat portion (199) is adapted to receive and seat the tip portion (122) of the needle member (120) thereby ensuring that the tip portion (122) of the needle member (120) is rested within the safety clip (114) and preventing misalignment of the needle member (120) during withdrawal from the catheter hub (102) or during disposal of the needle member (120).

In an embodiment, the length of the first resilient arm (172) is larger than the length of the second resilient arm (178). Such a construction of the arms (172, 178) may be provided to ensure that sufficient biasing force is exerted onto the interlocking flanges (116), thereby ensuring that the safety pin (114) is retained within the body portion (106). Also, asymmetric lengths of the arms may ensure contact of each connecting portion (184, 185) on the body (192) of the needle member (120) about the same plane A-A' [more clearly shown in FIG. 9A]. Such an engagement ensures uniform stress-distribution on the needle member (120), thereby preventing damage during assembly. In an embodiment, the needle member (120) may be assembled into the catheter hub (102) in the body portion (106) by initially flexing the arms (172, 178) and thereafter inserting the needle member (120) through the tubular sleeve (124).

Further, each of the bracket (170), the first and the second resilient arms (172, 178) may be defined with at least one rib member (190). The rib member (190) acts as a reinforcement to the safety clip (114), and thus improves its overall strength characteristics. As an example, the rib member (190) may extend about the surface of the bracket (170). Also, the rib member (190) may extend along the second section (176) of the first and the second arms (172, 178), which inherently improves the strength of the second section (176). The length of extension of the rib member (190) may be considered based on the strength or rigidity requirements of the safety clip (114). In an embodiment, the rib member (190) may be formed on the bracket (170) and/or the arms via conventional manufacturing techniques such as punching and the like.

In an embodiment, the rib member (190) may be provided on the bracket (170) as a reinforcement, in order to prevent damage to the bracket (170) via contact of a protuberance (194) provided on the needle member (120), during removal of the needle within the safety clip (114) upon withdrawal. In another embodiment, the rib member (190) may be made of a metallic material, a plastic material or a composite material or any other material which serves the purpose of providing reinforcement to the safety clip (114).

In an embodiment, the bracket (170), the first and the second arms (172, 178) may be made of metallic material or any other material which serves the purpose of ensuring interlocking with the body portion (106) when the needle member (120) is present within the catheter hub (102), and arrests the tip portion (122) within, when the needle member (120) is withdrawn from the catheter hub (102).

Figure 10:
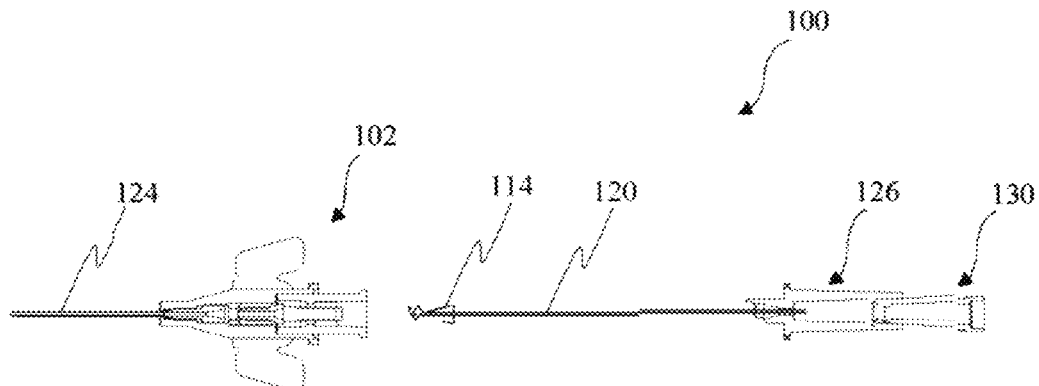
FIG. 10 is a sectional view of the cannula, when the needle member is withdrawn from the catheter hub, according to an exemplary embodiment of the present disclosure.

FIG. 10 illustrates a sectional view of the intravenous cannula (100) showing an operation for vein puncturing, according to an exemplary embodiment of the present disclosure. When the needle member (120) is passed through the co-axial recess (148) of the catheter hub (102) and via the actuator member (154), the needle member (120) is adapted to pierce through the slits (150) of the tubular valve member (140). After piercing the slits (150) of the valve member (140), the needle member (120) passes through the catheter tube (136) for puncturing the vein of the patient.

When the needle member (120) is withdrawn after puncturing the vein, the slits (150) of the tubular valve member (140) will close automatically since the tubular valve member (140) is made of flexible material which can self-close the opening at the slits (150) of the flat portion (144) of the valve member (140). Additionally, once the tip portion (122) of the needle member (120) is withdrawn from the proximal end (102a), particularly, beyond each connecting portion (184, 185) of the arms (172, 178) of the safety clip (114), the biasing force acting on the arms (172, 178) due to contact with the needle member (120) ceases. As such, the arms retract to an unbiased condition (119) [for e.g. as shown in FIG. 9B], during which the curved lip (188) completely closes the path for the tip portion (122) to move forward and beyond the safety clip (114). Thus, the safety clip (114) retains the needle member. (120) upon withdrawal from the catheter hub (102). In this scenario, the safety clip (114) may be withdrawn from the body portion (106) along with needle member (120) via the needle hub (126).

Also, the tip portion (122) rests on the seat portion (199) configured on the safety pin (114), and thus the alignment of the needle member (120) is maintained, irrespective of movement of the needle member (120) during withdrawal. Therefore, exposure of the tip portion (122) of the needle member (120) is prevented, thereby avoiding needle stick injury to the operator or to the patient. In an embodiment, the tip portion (122) may selectively rest on any of the seat portion (199) configured on the first and the second arms (172, 178).

Advantages

The disclosed needle guard assembly (104) including the safety clip (114) ensures that the tip portion (122) is retained within the safety clip (114), thereby preventing exposure of the tip portion (122) during withdrawal from the catheter hub (102) and thus preventing needle stick or needle prick injury to the user.

The disclosed valve closure member (162), upon pushing or closing the plurality of prongs (152) of the intravenous cannula (100), prevents an undesired reverse flow of blood from the vein of the patient when the actuator member (154) is displaced due to removal of the luer lock member.

The disclosed valve closure member (162) and the actuator member (154) may be activated or deactivated multiple times to allow flow of blood through the needle member (120) when a vein of the patient is punctured or to prevent undesired reverse flow of blood, with the efficacy of such flow/prevention of flow being similar in each activation or deactivation.

The disclosed plurality of prongs (152) of the valve member (140) being flexible when compared with the hardness of the valve closure member (162), the plurality of prongs (152) will close the slit by folding back by themselves automatically when the needle is withdrawn after puncturing of the vein is prevented.

The disclosed intravenous cannula prevents contact of blood of the patient to a user's hands since the reverse flow of the blood is prevented due to closing of the plurality of prongs (152) of the valve member (140) by the valve closure member (162), thereby preventing infections and diseases that may be caused due to the blood contact.

The disclosed intravenous cannula (100) is economical since the valve member (140), the actuator member (154) and the valve closure member (162) are made of plastic or bio-compatible material.

The disclosed intravenous cannula (100) provides an improved closing of the slits (150) of the valve member (140) since the plurality of prongs (152) of the valve member (140) is closed due to the pushing force acting towards the proximal end (136) of the catheter hub (102) of the user or operator by the valve closure member (162), thereby closing the passage without allowing reverse flow of blood.

LIST OF REFERENCE NUMERALS AND REFERENCE SIGNS

100 Intravenous Cannula
102 Catheter hub
102A Proximal end of catheter hub
102B Distal end of catheter hub
104 Needle guard assembly
106 Body portion
108 Projection of the body portion
110 Recess on the catheter hub
112 Bore in body portion
114 Safety clip
116 Interlocking flange
118 Biased condition of safety clip
119 Unbiased condition of safety clip
122 Cylindrical body portion
120 Needle member
122 Tip portion of the needle member
124 Tubular sleeve
126 Needle hub
128 Thumb grip
130 Flow control hub
132 Flashback chamber
134 Porous filter
136 Catheter tube
138 Annular stopper
140 Tubular valve member
142 Cylindrical portion
144 Flat portion
146 Protrusion
148 Co-axial recess
150 Slits -continued 152 Prongs
154 Actuator member
156 Flange
158 Convex surface
160 Circular recess
162 Valve closure member
164 First surface
166 Second surface
168 Through-hole
170 Bracket
172 First resilient arm
174 First section of first resilient arm
176 Second section of first resilient arm
178 Second resilient arm
180 First section of second resilient arm
182 Second section of second resilient arm
184 Connecting portion
186 Curved protrusion
188 Curved lip
190 Rib member
192 Body of needle member
194 Protuberance on needle member
196 Opening in bracket
198 Projection in connecting portion
199 Seat portion
A-A' Line of contact on body of needle member

The invention claimed is:

1. An intravenous cannula, comprising:
a catheter hub having a proximal end, a distal end and a first chamber;
an actuator member disposed within the first chamber and having an axial bore and an outer surface defining a recess, the actuator member configured to be axially displaced towards the distal end of the catheter hub to form a passage for fluid flow from the proximal end of the catheter hub to the distal end of the catheter hub when a luer lock member removably connected to the proximal end of the catheter hub displaces the actuator member;
a tubular valve member disposed within the first chamber and adapted to allow a needle member to pass through, the tubular valve member having a protrusion along an inner surface of the tubular valve member, the protrusion configured to engage with the recess on the outer surface of the actuator member, wherein an inner diameter of the tubular valve member is constant both distal and proximal to the protrusion, the tubular valve member defined with a flat portion at a first end, the flat portion configured with one or more slits defining a plurality of prongs, the one or more slits configured to allow the needle member to pass through for puncturing a vein of a subject,
wherein the plurality of prongs are displaced by the actuator member for fluid flow from the proximal end of the catheter hub to the distal end of the catheter hub when the luer lock member displaces the actuator member;
a valve closure member comprising a first surface at a proximal end defining a continuously and circumferentially extending surface having a concave or frusto-conical shape, a second surface at a distal end and a through-hole, the valve closure member disposed in the catheter hub such that the second surface abuts an undercut portion defined in the catheter hub and the first surface abuts the flat portion of the tubular valve member, wherein the valve closure member is adapted to displace the plurality of prongs to close the passage for fluid flow and preventing blood flow from the vein of the subject from the distal end of the catheter hub to the proximal end of the catheter hub when the luer lock member abutting the actuator member is removed; and a needle guard assembly, comprising:

a body portion connected to the proximal end of the catheter hub; and a safety clip biasing outwardly to lock onto at least one interlocking flange defined in the body portion, the safety clip in a biased position allowing the needle member to extend through the body portion and the catheter hub, wherein upon withdrawal of the needle member from the proximal end of the catheter hub, the safety clip disengages from the at least one interlocking flange and arrests a tip portion of the needle member within the safety clip, thereby preventing needle prick injury during withdrawal of the needle member from the catheter hub.

2. The intravenous cannula of claim 1, wherein the safety clip consists of:

a bracket defining an opening for receiving the needle member, the bracket adapted to be disposed within the body portion of the needle guard assembly;

a first resilient arm extending from one end of the bracket and having a connecting portion for engaging with the at least one interlocking flange of the body portion of the needle guard assembly and the needle member, the first resilient arm having a first section and a second section, such that dimensions of the first section are larger than the second section;

a second resilient arm extending from an opposing end of the bracket and having a connecting portion for engaging with the at least one interlocking flange of the body portion of the needle guard assembly and the needle member, the second resilient arm having a first section and a second section, such that dimensions of the first section are larger than the second section;

wherein the connecting portion of each of the first and second resilient arms is adapted to engage with the at least one interlocking flange and a body of the needle member when the needle member is extending through the catheter hub for puncturing the vein of the subject and disengage from the at least one interlocking flange and the body of the needle member when the needle member is withdrawn from the proximal end of the catheter hub.

3. The intravenous cannula of claim 2, wherein the connecting portion of each of the first and second resilient arms comprises:

a curved protrusion at a fore end, adapted to engage with the at least one interlocking flange of the body portion of the needle guard assembly; and a curved lip extending inwardly towards the bracket at an aft end, the curved lip adapted to engage on to the needle member, wherein the curved lip is adapted to arrest the tip portion of the needle member within the safety clip when the needle member is withdrawn from the proximal end of the catheter hub.

4. The intravenous cannula of claim 3, wherein the curved protrusion includes a projection extending towards the bracket, the projection along with each second section of the first and second resilient arms defining a seat portion, the seat portion adapted to receive and seat the tip portion of the needle member, thereby preventing misalignment of the needle member during withdrawal from catheter hub.

5. The intravenous cannula of claim 2, wherein a length of the first resilient arm is larger than a length of the second resilient arm.

6. The intravenous cannula of claim 2, wherein the bracket, the first resilient arm, the second resilient arm, or a combination thereof is defined with at least one rib member for reinforcement.

7. The intravenous cannula of claim 6, wherein the rib member is provided at a second section of the first and the second resilient arms as reinforcement.

8. The intravenous cannula of claim 2, wherein the needle member is configured with a protuberance defined proximal to its distal end, the protuberance adapted to engage with the bracket during withdrawal of the needle member from the proximal end of the catheter hub, thereby preventing retrieval of the needle member from the needle guard assembly.

9. The intravenous cannula of claim 1, wherein each of the at least one interlocking flange of the body portion of the needle guard assembly extends radially inwardly for ensuring engagement with the safety clip in its biased position, so that the safety clip is retained within the needle guard assembly.

* * * * *